(12) United States Patent
Willis et al.

(10) Patent No.: US 7,588,683 B2
(45) Date of Patent: Sep. 15, 2009

(54) COLUMN FOR LIQUID CHROMATOGRAPHY WITH ADJUSTABLE COMPRESSION

(75) Inventors: Frank M. Willis, Deptford, NJ (US); Clyde L. Machamer, Elkton, MD (US)

(73) Assignee: Agilent Technologies, Inc., Santa Clara, CA (US)

( * ) Notice: Subject to any disclaimer, the term of this patent is extended or adjusted under 35 U.S.C. 154(b) by 623 days.

(21) Appl. No.: 11/195,916

(22) Filed: Aug. 3, 2005

(65) Prior Publication Data

US 2007/0029241 A1    Feb. 8, 2007

(51) Int. Cl.
*B01D 15/08* (2006.01)
(52) U.S. Cl. .................... 210/198.2; 210/656
(58) Field of Classification Search ............ 210/198.2, 210/656, 659, 232, 450; 96/101, 106
See application file for complete search history.

(56) References Cited

U.S. PATENT DOCUMENTS

| | | | | |
|---|---|---|---|---|
| 3,504,799 A * | 4/1970 | Ogle | .................. | 210/198.2 |
| 4,026,803 A | 5/1977 | Abrahams et al. | | |
| 4,185,841 A * | 1/1980 | Brundage | .................... | 277/363 |
| 4,313,828 A | 2/1982 | Brownlee | | |
| 4,350,595 A * | 9/1982 | Gunkel | .................... | 210/656 |
| 4,557,830 A * | 12/1985 | Onitsuka et al. | ......... | 210/198.2 |
| 4,769,141 A * | 9/1988 | Couillard | .................. | 210/198.2 |
| 4,784,594 A | 11/1988 | Sharps, Jr. | | |
| 4,861,473 A | 8/1989 | Shackelford et al. | | |
| 5,188,730 A * | 2/1993 | Kronwald | ................. | 210/198.2 |
| 5,366,621 A * | 11/1994 | Bidell et al. | ............. | 210/198.2 |
| 5,378,361 A * | 1/1995 | Baeckstrum | ............. | 210/198.2 |
| 5,893,971 A * | 4/1999 | Shalon et al. | ............ | 210/198.2 |
| 5,919,361 A * | 7/1999 | Moran | ...................... | 210/198.2 |
| 6,387,256 B1 | 5/2002 | Tuvim | | |
| 6,527,951 B1 | 3/2003 | Tuvim | | |
| 6,679,989 B2 | 1/2004 | Willis et al. | | |
| 6,932,904 B2 * | 8/2005 | Laub et al. | ................ | 210/198.2 |
| 7,258,060 B2 * | 8/2007 | Dahl | ........................... | 92/194 |
| 2002/0179513 A1 | 12/2002 | Willis et al. | | |
| 2003/0173279 A1 * | 9/2003 | Aste | ........................ | 210/198.2 |
| 2003/0183566 A1 * | 10/2003 | Laub et al. | ............... | 210/198.2 |
| 2003/0194814 A1 * | 10/2003 | Shalon et al. | ............... | 436/161 |
| 2004/0182789 A1 * | 9/2004 | Gill et al. | .................... | 210/656 |
| 2005/0224414 A1 | 10/2005 | Izzo et al. | | |

FOREIGN PATENT DOCUMENTS

| | | |
|---|---|---|
| EP | 0 706 047 | 10/1996 |
| WO | WO 2004/024285 A1 | 3/2004 |
| WO | WO 2004/095019 | 11/2004 |

* cited by examiner

*Primary Examiner*—Ernest G Therkorn

(57) ABSTRACT

A column for liquid chromatography includes a chamber adapted to receive packing medium. Openings in the chamber allow fluid to pass through it. Porous plugs in the chamber retain the packing medium. A piston and one porous plug are movable within the chamber to compress the packing medium. A fitting engages the piston and is adjustably movable for moving the piston.

19 Claims, 4 Drawing Sheets

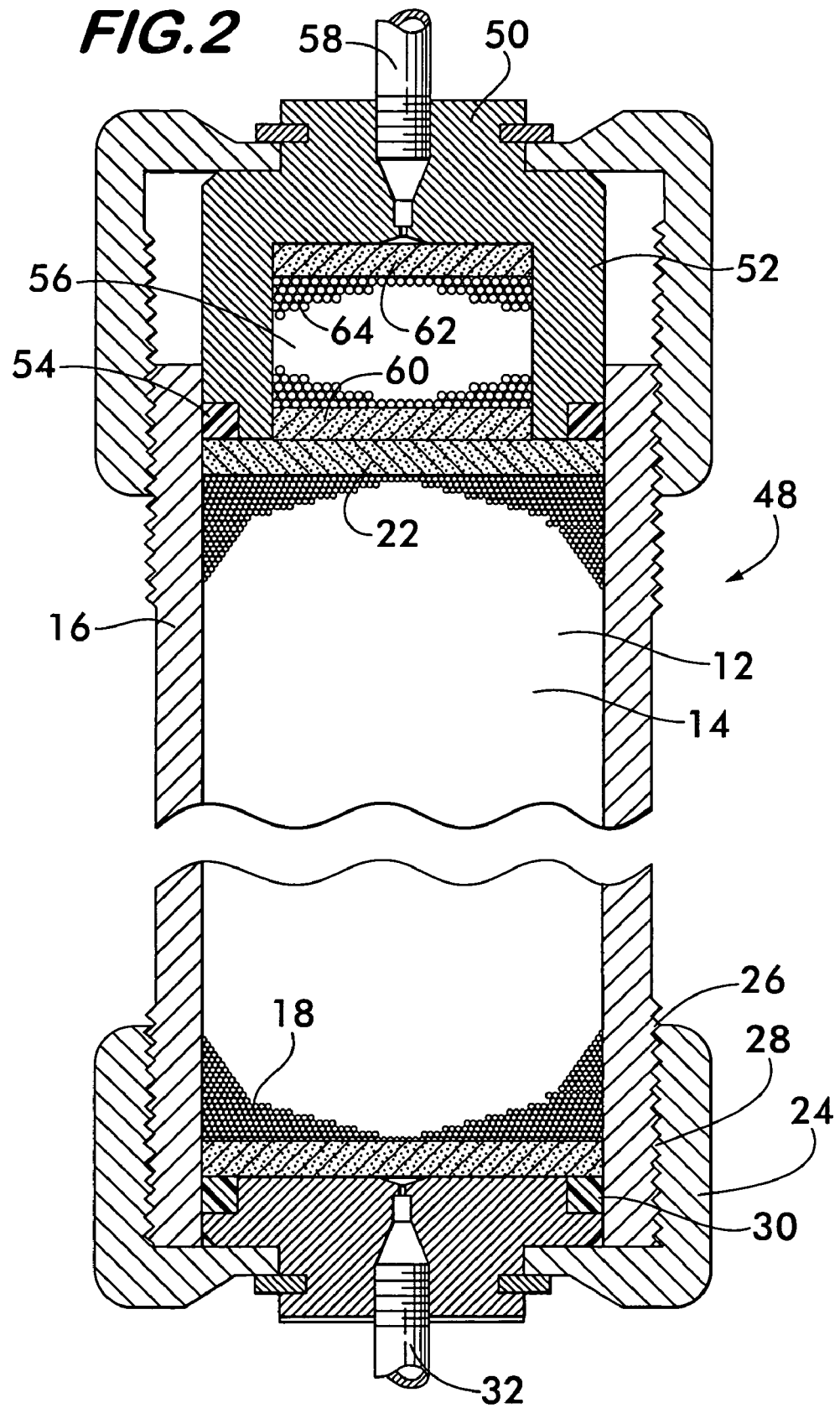

COLUMN FOR LIQUID CHROMATOGRAPHY WITH ADJUSTABLE COMPRESSION

BACKGROUND

High performance liquid chromatography (HPLC) is a process by which one or more compounds from a chemical mixture may be separated and identified. A transport liquid, for example a solvent, is pumped under high pressure through a column of packing medium, and a sample of the chemical mixture to be analyzed is injected into the column. As the sample passes through the column with the liquid, the different compounds, each one having a different affinity for the packing medium, move through the column at different speeds. Those compounds having greater affinity for the packing material move more slowly through the column than those having less affinity, and this speed differential results in the compounds being separated from one another as they pass through the column.

The transport liquid with the separated compounds exits the column and passes through a detector, which identifies the molecules, for example by spectrophotometric absorbance measurements. A two dimensional plot of the detector measurements against elution time or volume, known as a chromatogram, may be made, and from the chromatogram the compounds may be identified.

For each compound, the chromatogram displays a separate curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, are undesirable as they may allow minor components of the mixture to be masked by major components and go unidentified.

The uniformity of the packing medium within the column has a significant effect on column performance. It is desired that the particles comprising the packing medium be perfectly arranged and completely homogeneous so that the transport liquid and the sample mixture move at uniform rates through the column. Areas of loose packing medium create channels causing locally increased flow rates while areas that are partially plugged due to particle aggregation create eddies that retard the flow. Such local variations in the flow rate caused by non-uniform packing medium result in transport liquid mixing that degrades the column performance resulting in broadening of the peaks and a concomitant decrease the resolving capability of the HPLC apparatus.

Columns for HPLC are packed with packing media comprising, for example, silane derivatized silica spheres having a diameter less than 20 microns. Packing is performed at high pressures, typically between 7,000 and 9,000 psi, three to four times the pressure at which the column will operate. Under such high pressures, the columns, made from thick wall steel tubing, will expand radially as much as five packing particle diameters depending upon the ratio of wall thickness to inner diameter. Upon completion of packing, the pressure is removed and the remaining column components are installed. Removal of the pressure allows the column to relax and contract radially to its nominal diameter. This places the packing media under compression, and the hydraulically oriented layers of packing media buckle and shift in response. The buckling action disrupts the uniformity of the layers which adversely affects column performance. There is clearly a need for an HPLC column which does not suffer disruption of the hydraulic orientation of the packing media upon removal of the pressure imposed during packing.

SUMMARY OF THE INVENTION

The invention concerns a column for liquid chromatography. The column is adapted to contain a packing medium and comprises a chamber for receiving the packing medium. Preferably, the chamber is in the form of an elongated tube defining an axial bore. A first opening is positioned in the chamber for passing liquid through the chamber. A first porous plug, for example a frit formed of porous stainless steel, is positioned overlying the first opening for retaining the medium within the chamber. A second porous plug, also for retaining the medium within the chamber, is movable within the chamber. A piston is in facing relation with the second porous plug. The piston is movable within the chamber for compressing the second porous plug against the medium. A second opening, positioned in the piston, cooperates with the first opening and allows liquid to pass through the chamber. A fitting is mounted on the chamber and engages the piston. The fitting is adjustably movable for moving the piston within the chamber.

Preferably, the first and second porous plugs interfit within the bore with an interference fit. A seal is mounted on the piston and positioned between a surface of the piston and the bore of the tube. The seal is preferably an extrusion type seal. A thrust bearing is positioned between the fitting and the piston.

The piston may also comprise a chamber positioned between the piston opening and the second porous plug. A third porous plug is positioned within the chamber adjacent to the opening. A fourth porous plug is positioned within the chamber in spaced relation away from the third porous plug. The chamber is adapted to receive the packing medium between the third and fourth porous plugs. The piston thereby acts as a movable guard column.

The invention also includes a method of packing a high performance liquid chromatography column with a packing medium. The method comprises the steps of:

securing a first porous plug within a bore of the column, the first porous plug for retaining the packing medium within the column;

filling the bore with the packing medium;

positioning a movable porous plug within the bore so as to engage the packing medium;

positioning a movable piston within the bore so as to engage the movable porous plug;

pressurizing the bore;

moving the piston into the bore, thereby moving the movable porous plug and compressing the packing medium;

holding the piston in position compressing the packing medium; and depressurizing the bore.

BRIEF DESCRIPTION OF THE DRAWINGS

FIG. 2 is a longitudinal sectional view of an alternate embodiment of an HPLC column according to the invention.

DETAILED DESCRIPTION OF PREFERRED EMBODIMENTS

Figure 1:
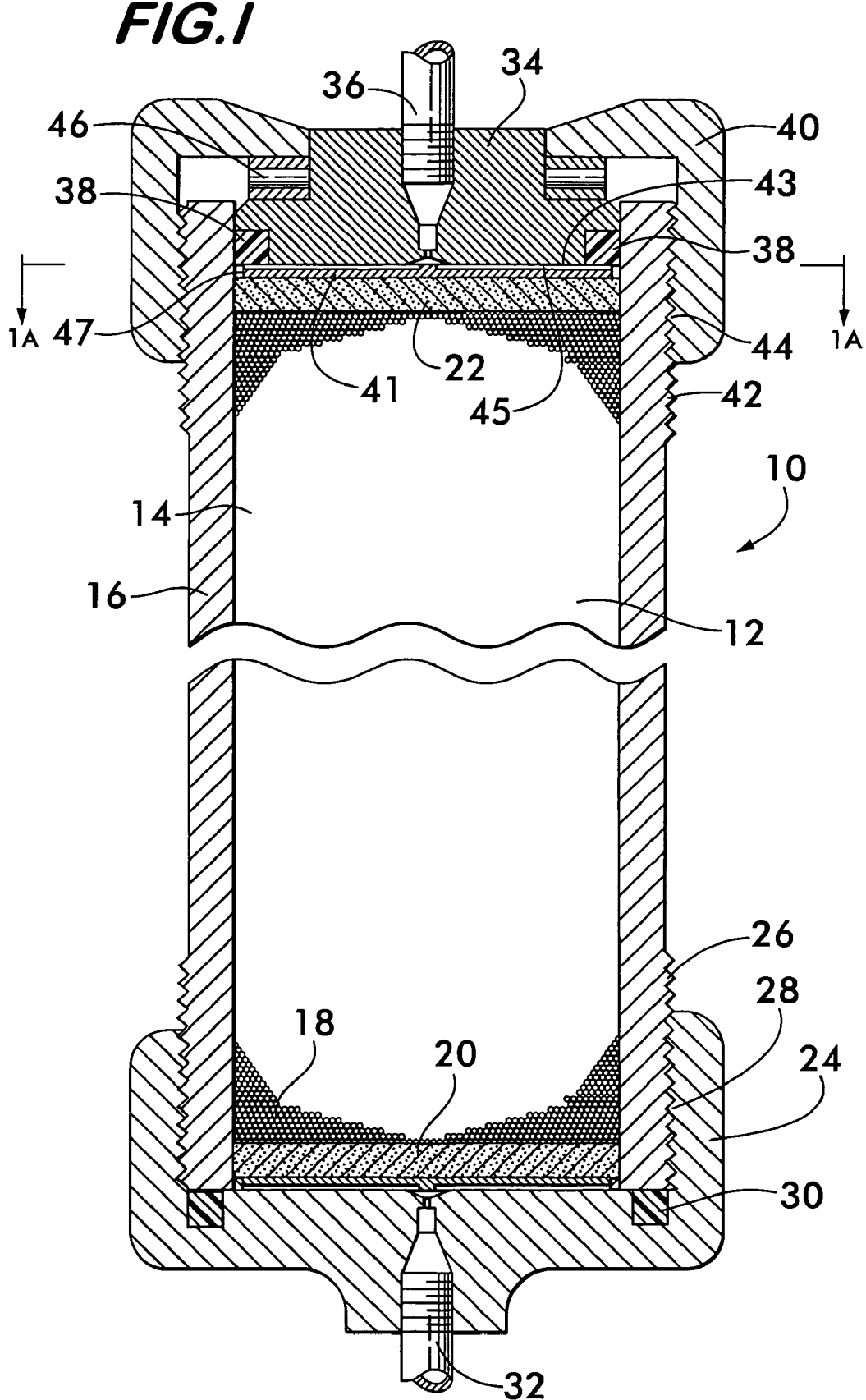
FIG. 1 is a longitudinal sectional view of an HPLC column according to the invention.

FIG. 1 shows a longitudinal sectional view of an HPLC column 10 according to the invention. Column 10 may be any type of column used in liquid chromatography, for example, an analytical column, a preparatory column or a guard column. The column 10 comprises a chamber 12, preferably defined by the axial bore 14 of an elongated tube 16. A packing medium 18, for example, silane derivatized silica spheres having a diameter less than 20 microns, is received within the bore 14. The medium is captured between porous plugs 20 and 22 which are press fit within the bore 14. Plugs 20 and 22 are preferably sintered stainless steel frits that allow the transport liquid and the analysis sample to pass while retaining the packing medium in place. The plugs 20 and 22 are pressed into bore 14 with an interference fit typically between 0.004 and 0.006 inches depending on the size of the column and the operating pressure. This degree of interference fit allows the plugs to seal against the inner surface of tube 16 and prevent leakage of the packing medium while allowing the plugs to move axially within the bore. The press fit of the plugs eliminates the need for additional seals which would increase the cost of the column and decrease its performance by causing dead space that would promote mixing of the transport liquid.

In the example column embodiment of FIG. 1, plug 20 is supported within bore 14 by a fitting 24 that is attached to the tube 16 by complementary threads 26 and 28 on the outer surface of tube 16 and the inner surface of the fitting 24 respectively. A seal 30 is positioned between tube 16 and the fitting 24 to prevent leakage of the transport liquid. Fitting 24 has an opening 32 that is in fluid communication with the bore 14 through the porous plug 20. Opening 32 allows the transport liquid to pass through the column 10, and may serve as either an inlet or an outlet. In this example, opening 32 in fitting 24 is the column outlet. Opening 32 is adapted to connect to capillary tubing for integration of the column 10 into a high performance liquid chromatograph (not shown).

Porous plug 22 is engaged with a piston 34 that is movable within axial bore 14. Piston 34 has an opening 36 in fluid communication with the bore through plug 22. Opening 36 is also adapted to connect to capillary tubing for integrating the column into a high performance liquid chromatograph. In this example column, opening 36 serves as the inlet to the column, but in alternate embodiments it could also be an outlet.

A seal 38 is positioned between the piston 34 and the inner surface of tube 16. Seal 38 is preferably formed of perfluoroelastomeric material marketed under the trade names CHEMRAZ and KALREZ. Seal 38 is preferably rectangular in cross section and operates as an "extrusion" type seal which seals more tightly without overstressing the seal material by deformation when subjected to increased pressure within bore 14. Seal 38 operates effectively when two of its surfaces are in contact with the two parts which are to be sealed (in this example, piston 34 and tube 16), and the space between the parts is sufficiently small so as to prevent extrusion of the seal between them when subjected to pressure.

Piston 34 is captured within axial bore 14 by a fitting 40. Fitting 40 is attached to the tube 16 by threads 42 on the tube that engage complementary threads 44 on the fitting 40. A thrust bearing 46 is positioned between the fitting 40 and the piston 34 to reduce the friction between the piston and the fitting as the fitting is turned. The thrust bearing is preferably a roller type bearing but may alternately comprise a Teflon washer. Rotation of the fitting 40 forces the piston 34 and the porous plug 22 into axial bore 14 to compress the packing medium 18 as described below.

Figure 1A:
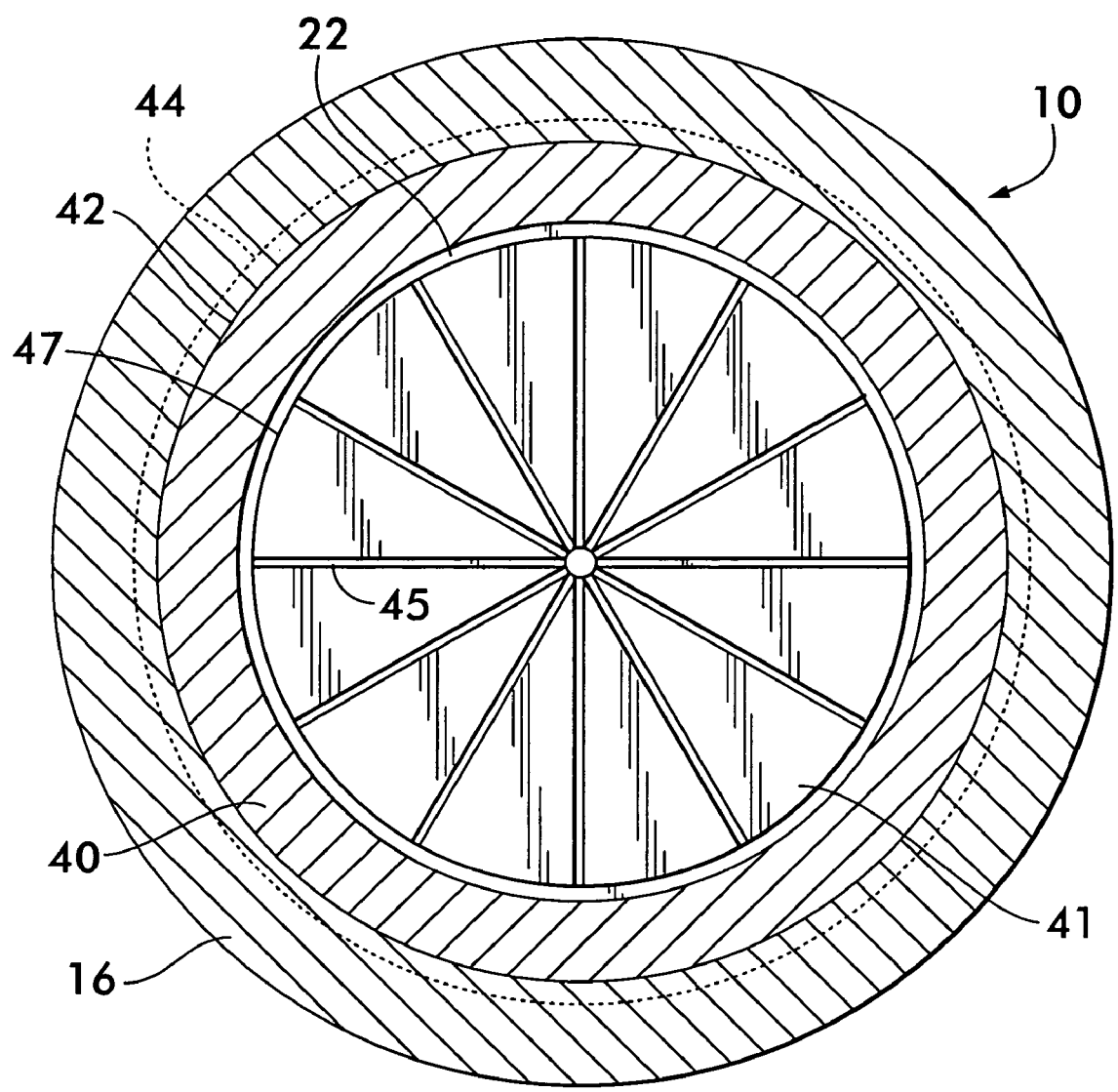
FIG. 1A is a cross sectional view of the column shown in FIG. 1 taken at line 1A-1A.

A flow distribution disk 41 may be positioned between the piston 34 and the porous plug 22. The disk, best shown in FIG. 1A, has a plurality of radially extending channels 45 and acts as a baffle plate to conduct liquid flowing into column 10 to the circumference 47 of the disk. Disk 41 facilitates a more uniform flow of liquid through the column by initially directing the flow away from the center of the column and thereby counteracting the natural tendency of the fluid to flow faster through the center of the tube 16 than the flow adjacent to the inner surface of the bore.

The various components described above are made from materials that are inert to organic solvents comprising the transport liquid as well as to the compounds comprising the analysis sample. Furthermore, the materials must have sufficient strength to withstand the high pressures (12,000 psi and greater) at which the columns are prepared and operated. Stainless steel is a preferred material for the tube 16, the porous plugs 20 and 22, the piston 34 and the fittings 24 and 40 because it has both the properties of inertness and high strength.

The movable piston 34 and porous plug 22 will provide an improvement in column stability and performance by permitting precise control of the compression of the packing medium 18 within the tube 16 during column preparation and use, as described in the examples provided below.

With respect to column preparation, porous plug 20 is pressed into bore 14 of tube 16. Fitting 24 with seal 30 is threaded onto the tube to support the plug 20 and engage the seal with the tube in sealing engagement. The packing medium 18 is loaded into axial bore 14 and the porous plug 22 is press fit into the bore 14 providing some initial compression to the packing medium. Piston 34 (with seal 38) is then inserted into the bore and fitting 40 is threaded onto tube 16 into engagement with the piston 34. Column 10 is then connected to a high pressure flushing pump via inlet and outlet openings 36 and 32 and subjected to high internal pressure. This causes the tube to expand radially, and the packing medium 18 is arranged into hydraulically oriented layers supported against porous plug 20. While the tube is under pressure from the high pressure flushing pump, fitting 40 is tightened, using a tool if required, to force the piston 34 into the axial bore 14 and force the porous plug 22 against the medium 18. Fitting 40 is tightened sufficiently to capture and hold the packing compression of the medium and the volume expansion of the tube under the high pressure of the flushing pump. By compressing the packing medium when the tube is expanded under pressure using the movable piston and porous plug, the tube is prevented from relaxing and returning to its nominal diameter once the pressure is removed. The hydraulic orientation of the packing medium attained during the high pressure flush is thus preserved, providing a stable, uniform bed of packing medium to maximize column performance.

An alternate packing method using the movable piston and porous plug would include the steps of loading the column 10 with packing medium under pressure, removing the pressure and pressing the porous plug 20 into the axial bore 14 to restore the lost packing compression, and then inserting piston 34 into the bore and tightening the fitting 40 to a predetermined torque to maintain the packing medium compression.

In another method, the column is again loaded under pressure, the pressure is removed, and the porous plug is press fit into the axial bore into contact with but not compressing the packing medium. The piston is then inserted into the bore and the fitting 40 is tightened to restore the packing medium compression lost when the pressure was removed to install the porous plug and the piston.

To facilitate the packing methods described above, the pitch of threads 42 and 44 can be chosen to provide a convenient rate of advance of piston 34 with rotation of fitting 40. For example, 20 threads per inch would yield a piston advance rate of 0.005 inches per 30 degrees of fitting rotation. A fixed circumferential degree scale could be added to the outer surface of tube 16, the scale being used with an index mark positioned on fitting 40 to facilitate precision and reproducibility of the packing medium compression.

The movable piston and porous plug may also be used to restore packing material compression as the bed of packing material degrades over time. When decreased column performance is detected, for example by broadening of peaks on a chromatogram, the fitting 40 may be tightened to increase the compression of the packing material and thereby eliminate areas of loose packing material detrimental to column performance.

FIG. 2 shows an embodiment of an HPLC column 48 according to the invention wherein the piston 50 includes a guard column 52. Guard columns are positioned upstream of analytical and preparatory columns and are used to trap impurities or particulates in the analysis sample or the transport liquid that may foul the downstream column and degrade its performance and shorten its useful life.

Similar to the embodiment described above, piston 50 is movable within axial bore 14 of tube 16 and carries a seal 54 preventing transport fluid leakage. Piston 50 engages porous plug 22, which is press fit and movable within the bore 14. The piston 50 also has a chamber 56 positioned between its inlet opening 58 and the porous plug 22. Additional porous plugs 60 and 62 are positioned within the chamber 56 in spaced relation to one another defining a space wherein packing medium 64 of the guard column is contained. It is noted that the chamber 56 of the guard column 52 is directly coupled in a through-bore arrangement with axial bore 14 as disclosed in U.S. Pat. No. 6,679,989. Such an arrangement reduces the potential for mixing of the transport liquid as it passes from the guard column into the bore 14 by avoiding an abrupt change in the cross sectional area of the flow path through the column. Mixing of the transport liquid is preferably avoided because it degrades column performance.

Figure 3:
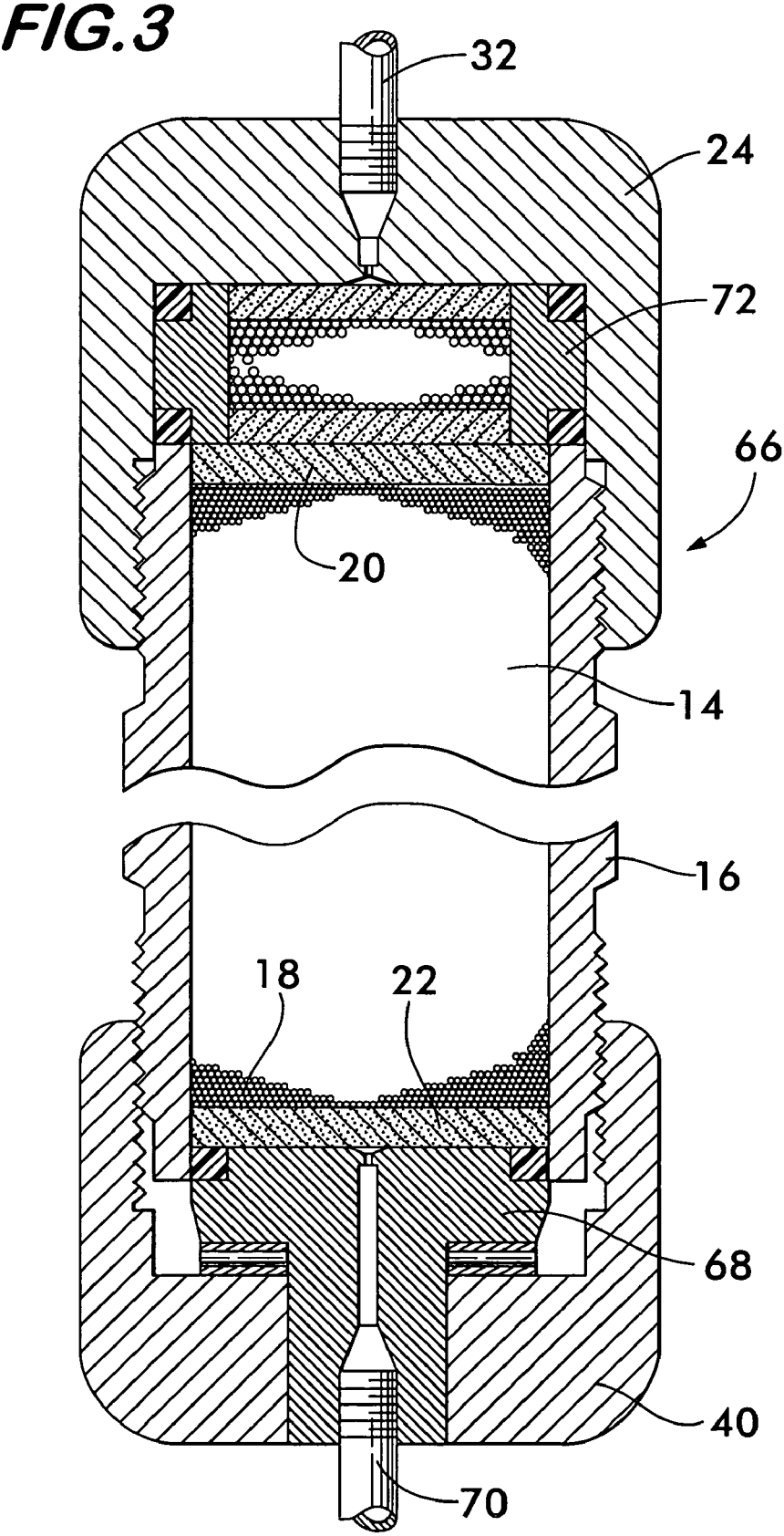
FIG. 3 is a longitudinal sectional view of another embodiment of an HPLC column according to the invention.

Another embodiment of an HPLC column 66 according to the invention is shown in FIG. 3. Column 66 has a movable piston 68 with an opening 70 that forms the outlet from the column. Outlet opening 70 is in fluid communication with the axial bore 14 of tube 16 through the movable porous plug 22 press fit within the bore. Fitting 40 is threadedly engaged with tube 16 and rotation of the fitting moves the piston 68 and the porous plug 22 to compress the packing medium 18 similarly to the embodiments described above. A guard column 72 is positioned at the opposite end of the tube 16 between the fitting 24 and the porous plug 20. In this embodiment, opening 32 of fitting 24 forms the inlet to the column.

An HPLC column having a means for compressing the bed of packing medium is disclosed in published International Application Number WO 2004/024285, entitled "A Chromatographic Column and Methods for Controlling Sorbent Density". This publication discloses a column that employs a fixed protruding inlet filter assembly for controlling sorbent bed density. Being fixed, unlike the piston disclosed and claimed herein, the aforementioned inlet filter assembly is not adjustable and thus cannot compensate for degrading column performance due to disruption of the hydraulic orientation of the packing medium or restore packing medium compression as the bed of packing medium deteriorates over time.

What is claimed is:

1. A column for liquid chromatography, said column adapted to contain a packing medium, said column comprising:
   a chamber for receiving said packing medium, said chamber defining an axial bore having a diameter;
   a first opening positioned in said chamber for passing liquid through said chamber;
   a first porous plug positioned overlying said first opening for retaining said medium within said chamber, said first porous plug having a diameter greater than said diameter of said axial bore;
   a second porous plug for retaining said medium within said chamber, said second porous plug being movable within said chamber, said second porous plug having a diameter greater than said diameter of said axial bore;
   a piston in facing relation with said second porous plug, said piston being axially movable within said axial bore of said chamber for compressing said second porous plug against said medium;
   a second opening, positioned in said piston, for passing liquid through said chamber; and
   a fitting rotatably mounted on an outer surface of said chamber and engaging said piston, said fitting being adjustably movable for axially moving said piston within said chamber.

2. A column according to claim 1, wherein said chamber comprises an elongated tube.

3. A column according to claim 2, wherein said interference fit comprises a means for sealing the respective first and second porous plugs against an inner surface of the bore of the chamber can prevent leakage of the packing medium and allowing for selective axial movement of the second porous plug.

4. A column according to claim 2, further comprising a seal mounted on said piston and positioned between a surface of said piston and said bore of said tube.

5. A column according to claim 4, wherein said seal comprises an extrusion type seal.

6. A column according to claim 1, wherein said first and second porous plugs comprise frits.

7. A column according to claim 1, further comprising a thrust bearing positioned between said fitting and said piston.

8. A column according to claim 1, further comprising a guard column positioned between said first porous plug and said first opening, said guard column comprising:
   a chamber for receiving said packing medium;
   a third porous plug positioned between said first opening and said packing medium; and
   a fourth porous plug positioned between said packing medium and said first porous plug.

9. A column for liquid chromatography, said column adapted to contain a packing medium, said column comprising:
   an elongated tube defining an axial bore for receiving said medium, the axial bore having a diameter;
   an outlet opening at one end of said tube in fluid communication with said bore for discharging liquid therefrom;
   a first porous plug overlying said outlet opening for retaining said medium within said bore;
   a second porous plug positioned proximate to an opposite end of said tube and movable axially within said bore toward said first porous plug, wherein at least one of the first and second porous plugs has a diameter at least 0.004 inches larger than the diameter of the axial bore;
   a piston positioned proximate to said opposite end of said tube in facing relation with said second porous plug, said piston being movable axially within said bore for compressing said second porous plug against said medium;

an inlet opening positioned within said piston for admitting liquid to said bore; and a fitting mounted on said opposite end of said tube and engaging said piston, said fitting being adjustably tightenable, said piston being moved into said bore and compressing said second porous plug axially against said medium upon tightening of said fitting.

10. A column according to claim 9, wherein said interference fit comprises a means for sealing the respective first and second porous plugs against an inner surface of the bore of the chamber can prevent leakage of the packing medium and allowing for selective axial movement of the second porous plug.

11. A column according to claim 9, wherein said piston comprises a chamber positioned between said inlet opening and said second porous plug, a third porous plug being positioned within said chamber adjacent to said inlet opening, a fourth porous plug being positioned within said chamber in spaced relation away from said third porous plug, said chamber being adapted to receive said packing medium between said third and fourth porous plugs.

12. A column according to claim 11, further comprising a seal mounted on said piston and positioned between a surface of said piston and said bore of said tube.

13. A column according to claim 12, wherein said seal comprises an extrusion type seal.

14. A column according to claim 9, further comprising a flow distribution disk positioned between said piston and said second porous plug, said flow distribution disk having a surface facing said inlet opening, said surface having a plurality of radially oriented channels for directing flow of liquid from said inlet opening outwardly towards the circumference of said disk.

15. A column for liquid chromatography, said column comprising:

an elongated tube defining an axial bore having a diameter;

a first fitting removably attached to one end of said tube;

an outlet opening positioned in said first fitting in fluid communication with said bore;

a first porous plug positioned within said bore overlying said outlet opening;

a second porous plug positioned within said bore in spaced apart relation from said first porous plug, wherein at least one of the first and second porous plugs has a diameter at least 0.004 inches larger than the diameter of the axial bore;

a packing medium positioned within said bore between said first and said second porous plugs;

a piston axially movable within said bore and engaged with said second porous plug for compressing said second porous plug against said packing medium;

an inlet opening positioned within said piston in fluid communication with said bore; and a second fitting mounted on an opposite end of said tube and engaged with said piston, said second fitting being threadedly engaged with said tube and rotatable for moving said piston within said bore to compress said packing medium therein.

16. A column according to claim 15, wherein said first and second porous plugs comprise frits.

17. A column according to claim 15, wherein said piston comprises a chamber positioned between said inlet opening and said second porous plug, a third porous plug being positioned within said chamber adjacent to said inlet opening, a fourth porous plug being positioned within said chamber in spaced relation away from said third porous plug, said chamber containing said packing medium between said third and fourth porous plugs.

18. A column according to claim 17, further comprising an extrusion type seal mounted on said piston and positioned between a surface of said piston and said bore of said tube.

19. A column according to claim 17, further comprising a thrust bearing positioned between said fitting and said piston.

* * * * *

UNITED STATES PATENT AND TRADEMARK OFFICE
CERTIFICATE OF CORRECTION

PATENT NO. : 7,588,683 B2  Page 1 of 1
APPLICATION NO. : 11/195916
DATED : September 15, 2009
INVENTOR(S) : Frank M. Willis et al.

It is certified that error appears in the above-identified patent and that said Letters Patent is hereby corrected as shown below:

In the Claims:

In column 6, line 7, in Claim 1, delete "medium, said" and insert -- medium, the --, therefor.

In column 6, lines 12-14, in Claim 1, delete "chamber, said first porous plug having a diameter greater than said diameter of said axial bore;" and insert -- chamber; --, therefor.

In column 6, lines 17-18, in Claim 1, delete "said second porous plug having a diameter greater than said diameter of said axial bore;" and insert -- wherein at least one of the first and second porous plugs has a diameter at least 0.004 inches larger than the diameter of the axial bore; --, therefor.

In column 6, line 20, in Claim 1, delete "within said" and insert -- within the --, therefor.

Signed and Sealed this

Twenty-sixth Day of October, 2010

David J. Kappos
*Director of the United States Patent and Trademark Office*